United States Patent [19]
Rakestraw et al.

[11] Patent Number: 5,942,093
[45] Date of Patent: Aug. 24, 1999

[54] ELECTRO-OSMOTICALLY DRIVEN LIQUID DELIVERY METHOD AND APPARATUS

[75] Inventors: David J. Rakestraw, Fremont; Deon S. Anex, Livermore; Chao Yan, Pleasanton; Rajeev Dadoo; Richard N. Zare, both of Stanford, all of Calif.

[73] Assignee: Sandia Corporation, Livermore, Calif.

[21] Appl. No.: 08/878,470

[22] Filed: Jun. 18, 1997

[51] Int. Cl.[6] .................................................. G01N 27/00
[52] U.S. Cl. ......................... 204/450; 204/600; 204/601; 204/603; 204/604
[58] Field of Search .................................. 204/450, 600, 204/601, 603, 604

[56] References Cited

U.S. PATENT DOCUMENTS

| | | | |
|---|---|---|---|
| 5,378,334 | 1/1995 | Dadoo et al. | 204/180.1 |
| 5,441,613 | 8/1995 | McCormick et al. | 204/180.1 |
| 5,545,303 | 8/1996 | Schasfoort et al. | 204/601 |
| 5,573,651 | 11/1996 | Dasgupta et al. | 204/601 |
| 5,585,069 | 12/1996 | Zanzucchi et al. | 204/600 X |

*Primary Examiner*—Arun S. Phasge
*Attorney, Agent, or Firm*—Timothy Evans; Kurt Olsen

[57] ABSTRACT

Method and apparatus for controlling precisely the composition and delivery of liquid at sub-$\mu$L/min flow rate. One embodiment of such a delivery system is an electro-osmotically driven gradient flow delivery system that generates dynamic gradient flows with sub-$\mu$L/min flow rates by merging a plurality of electro-osmotic flows. These flows are delivered by a plurality of delivery arms attached to a mixing connector, where they mix and then flow into a receiving means, preferably a column. Each inlet of the plurality of delivery arms is placed in a corresponding solution reservoir. A plurality of independent programmable high-voltage power supplies is used to apply a voltage program to each of the plurality of solution reservoirs to regulate the electro-osmotic flow in each delivery arm. The electro-osmotic flow rates in the delivery arms are changed with time according to each voltage program to deliver the required gradient profile to the column.

13 Claims, 3 Drawing Sheets

ELECTRO-OSMOTICALLY DRIVEN LIQUID DELIVERY METHOD AND APPARATUS

STATEMENT OF GOVERNMENT INTEREST

This invention was made with Government support under contract no. DE-AC04-94AL85000 awarded by the U.S. Department of Energy to Sandia Corporation. The Government has certain rights in the invention.

CROSS REFERENCE TO RELATED APPLICATIONS

Not Applicable.

FIELD OF THE INVENTION

This invention relates generally to method and apparatus for the precise delivery of liquids having controlled composition and more particularly, to an electro-osmotically driven system for controlling precisely the composition and delivery of a liquid at low flow rates.

BACKGROUND OF THE INVENTION

In many applications ranging from medical analysis to environmental detection, the precise delivery of a liquid of known but varying composition is important. The delivery of such a liquid at low flow rates is useful in some applications such as those involving capillary separation. One field of application is liquid chromatography.

In liquid chromatography, chemical separations may be performed by flowing a fluid (the mobile phase) past an immobilized material (the stationary phase) inside a liquid chromatography (LC) column. This technique is used for chemical analysis by injecting a sample consisting of multiple components into one end of the LC column, allowing them to be separated into distinct bands as the sample flows through the LC column, and detecting those bands near the exit end of the LC column. In those systems, the separation is governed by the dynamic partitioning of the analyte between the mobile phase and the stationary phase. Control of the separation may be achieved by adjusting the composition of the mobile phase or the stationary phase or both to influence analyte partitioning.

High-performance liquid chromatography (HPLC), which is an established analytical technique, relies on high-pressure mechanical pumps to flow the mobile phase through the LC columns that are packed with immobilized particles. The stationary phase may comprise the particles themselves or particles with a chemical layer bonded to them. "Isocratic" separations are achieved by using a single pump to flow a mobile phase of constant composition through the packed LC column.

A. Capillary Analytical Methods

Several analytical methods using miniaturized or capillary columns have been developed, including capillary zone electrophoresis (CZE) and micro-HPLC. The CZE technique, in which a voltage potential is applied to a buffer-filled capillary to generate electro-osmotic flow, provides excellent efficiency in separating charged species via their different electrophoretic mobilities. In CZE, the capillary is typically made of silica, a material that forms fixed negative charges on the inner capillary wall in the presence of a solution of the correct pH containing electrolytes. Before the voltage gradient is applied, cations in the electrolyte solution will be attracted to these fixed negative charges, forming a so-called double layer at the capillary wall. Application of the voltage gradient creates a net movement of the cations loosely associated with the fixed negative charges at the electrolyte/silica interface. This movement, referred to as electro-osmotic flow, causes the bulk of the electrolyte solution to be dragged toward the negatively charged discharge outlet. A key disadvantage of the CZE approach, however, is that it cannot be used to resolve neutral compounds.

Micro-HPLC, on the other hand, employs a stationary phase material in a capillary column and provides high selectivity in a wide range of applications because of the variety of stationary phase materials available for HPLC. The column efficiency, however, is reduced in micro-HPLC because the mobile phase is driven through the capillary separation column using high mechanical pump pressure, which results in a parabolic flow velocity profile.

The emerging liquid chromatography technique known as capillary electrochromatography (CEC) combines the high selectivity of micro-HPLC and the high efficiency of CZE. In CEC, a capillary column is packed with a stationary phase material similar to that used in micro-HPLC. The mobile phase, however, is pumped through the capillary column using an applied electric field to create an electro-osmotic flow, similar to that in CZE, rather than using high pressure mechanical pumps. The CEC approach can thus achieve the high efficiency of CZE. In addition, as in the case with micro-HPLC, CEC may be used to analyze neutral compounds that are not separable by CZE. The miniaturization of the separation column by using a capillary column in CEC offers several advantages, including improved efficiency, mass detection sensitivity, low solvent consumption, small sample quantity, and easier coupling to detector such as mass spectrometers and flame-based detectors.

B. Gradient Elution

Gradient elution is a process by which the mobile phase composition is varied during separation for separating a wide variety of complex samples. The process has been developed for HPLC and micro-HPLC. The gradient elution approach is useful when the components of the mixture have a range of properties and no single mobile phase composition is appropriate for separating all of them.

In HPLC, the creation of the solvent gradient is accomplished by using two high-pressure mechanical pumps to deliver two different fluids into a small mixing chamber. The composition of the mobile phase is controlled and varied by adjusting the relative output flows from the individual pumps to achieve gradient elution.

In chemical analysis using electrokinetic techniques, such as CZE or CEC, current approaches include the use of mechanical means for gradient elution, such as the use of a pump or manual addition to a reservoir to deliver a gradient to a capillary column, or an electric field to deliver ionic species via electrophoresis to vary the composition in a separation column. For instance, one system uses a pressure-driven HPLC gradient system to deliver a solvent gradient to a packed capillary LC separation column. An applied electric potential is combined with pressure to perform the chromatographic separation. This technique is known as "pseudo-electrochromatography" or "pressure-assisted CEC." The key disadvantages of this method include slow response and low reliability at low flow rates.

Others have used different mechanical means for changing the mobile phase composition in a separation column during separation. A syringe-type doser has been used to pump the modifying electrolyte into the background electrolyte chamber to form pH gradients. Some have used a programmed solvent-delivery system and a split injector to generate pH gradients. Still others have proposed an HPLC gradient system to generate pH gradients and flow gradients in CZE. A stepwise gradient in micellar electrokinetic capillary chromatography (MECC) has been produced by manually pipetting aliquots of a gradient solvent containing 2-propanol into the inlet reservoir of the capillary. These systems have similar drawbacks as those of the pressure-assisted CEC system.

Another type of technique uses electric fields to generate pH gradients in isotachophoresis and capillary electrophoresis (CE). One such system employs two buffer chambers, each with its own electrode, to cause the migration of two different ionic species into the capillary during separation. The two buffer reservoirs are separated from the capillary by semipermeable membranes which allows ionic species to pass therethrough. This technique is appropriate for modifying the ionic content in a separation column. It cannot, however, be used for delivering an arbitrary flow.

Low volume flow rates of varying composition are required in capillary-based separation techniques when a single mobile phase is insufficient to separate all of the chemical components of a sample. Prior chromatography systems using miniature columns either are unable to employ gradient elution or use mechanical delivery means which produces gradients with parabolic flow velocity profiles and loss of separation efficiency. Conventional approaches of providing a variable composition mobile phase at low flow rates are expensive to implement, slow to respond to external control, and are generally unreliable in composition for flow rates of less than 1 $\mu$L/min. Although the miniaturization of separation columns in CEC offers the above-mentioned advantages, delivering a $\mu$L/min gradient flow into a capillary column (e.g., 10–100 $\mu$m i.d.) packed with micrometer-size particles poses a difficult problem. There is therefore a need for a liquid delivery system for controlling precisely the delivery and the composition of a liquid having varying composition at sub-$\mu$L/min flow rates.

SUMMARY OF THE INVENTION

It is a feature of this invention to provide an electro-osmotically driven system for the precise delivery of liquid having varying composition at sub-$\mu$L/min flow rates, preferably under computer control, such that the system is quickly responsive to changes in controlling voltage.

It is another feature of the invention to provide a system for performing solvent gradient elution in capillary chromatography.

It is another feature of the present invention to provide an apparatus and a method for performing gradient elutions using an electro-osmotically driven solvent gradient for capillary electrochromatography.

It is yet another advantage of this invention to generate dynamic solvent gradients with flow rates as low as the sub-$\mu$L/minute range without flow-pulsation and solvent-compressibility problems by merging at least two electro-osmotic flows that are independently regulated, preferably by computer-controlled voltages.

It is a further advantage of this invention to provide a system which can be readily automated and modified to generate a multi-solvent gradient not only for mobile phase composition purposes, but also for other types of gradients, and a system which can be readily coupled to other types of electrokinetic separation techniques in a capillary or narrow channel format, such as capillary zone electrophoresis, isotachophoresis, and isoelectric focusing.

One aspect of this invention is a liquid delivery system for the precise delivery of a liquid having varying composition at sub-$\mu$L/min flow rates which comprises a plurality of solutions and means for supplying a voltage profile to each of the solutions. One embodiment of said means comprises a plurality of variable high voltage power supplies each connected to one of the plurality of solutions and a programmable controller in communication with the plurality of variable high voltage power supplies. A mixing connector provides a mixing volume and includes a plurality of inlet orifices and an outlet orifice. The delivery system further includes a plurality of delivery arms. Each of the delivery arms has a delivery arm inlet in communication with one of the plurality of solutions and a delivery arm outlet connected to one of the inlet orifices of the mixing connector. Receiving means for receiving the solution output by the mixing connector can desirably be connected to the outlet orifice of the mixing connector. Preferably the receiving means is a column having a column inlet connected to the outlet orifice of the mixing connector.

Another aspect of the present invention is an electro-osmotically driven gradient system which comprises a plurality of solutions, a voltage controller, preferably a computer processor, and means in communication with the voltage controller for generating a plurality of voltage programs. Each of the plurality of voltage programs is applied to each of the plurality of solutions to produce a dynamic electro-osmotic flow from each of the plurality of solutions. The plurality of dynamic electro-osmotic flows are mixed in a mixing volume to form a dynamic gradient solution. The gradient system can include another means for delivering the dynamic gradient solution to an output column.

In accordance with yet another aspect of the present invention, a method for delivering a liquid with variable composition comprises the steps of generating a plurality of voltage programs. The plurality of voltage programs is applied to a plurality of solutions to generate a plurality of dynamic gradient profile flows of the plurality of solutions. The plurality of dynamic gradient profile flows are merged to produce a gradient solution. The gradient solution is delivered to an inlet of a receiving means, preferably an output column.

The present invention overcomes the significant deficiencies of prior gradient LC devices and produces resolution superior to HPLC at a significantly lower cost. The present system is a purely electro-osmotically driven system that permits reliable gradient elution from capillary columns at sub-$\mu$L/minute flow rates without the problems of flow-pulsation and solvent-compressibility commonly encountered in gradient HPLC. The system has superior performance, including faster response, higher reliability at low flows, and the ability to produce arbitrary gradient profiles, and can be used for a variety of applications.

BRIEF DESCRIPTION OF THE DRAWINGS

The preferred embodiments of this invention, illustrating all their features, will now be discussed in detail. These embodiments depict the novel and nonobvious system and method for generating electro-osmotically driven flows, which can be gradient flows, of this invention shown in the accompanying drawings, which are included for illustrative purposes only. These drawings include the following figures, with like numerals indicating like parts.

DETAILED DESCRIPTION OF THE INVENTION

Figure 1:
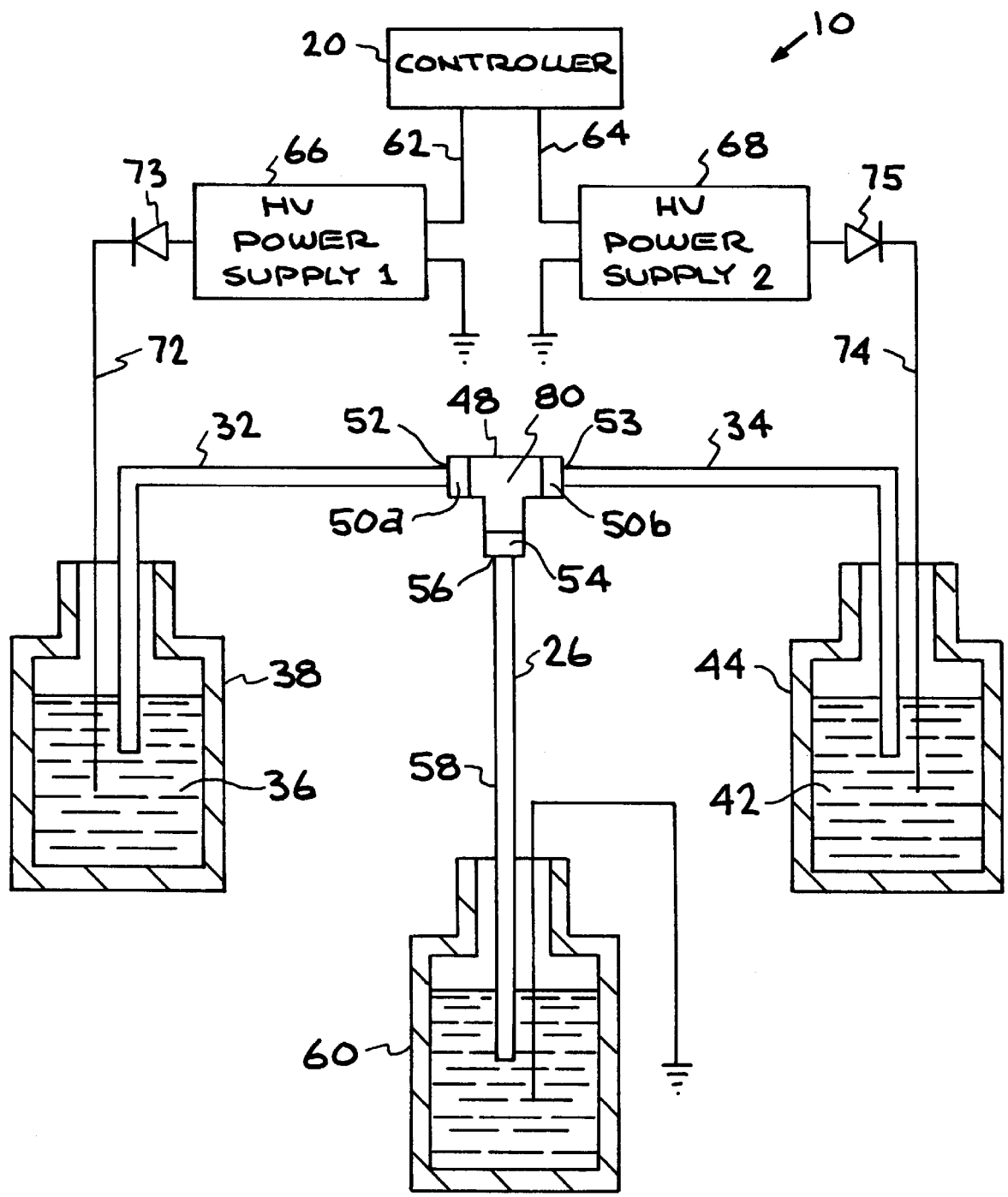
FIG. 1 is a schematic view of an exemplary embodiment of the solvent gradient delivery system of the present invention.
Figure 2:
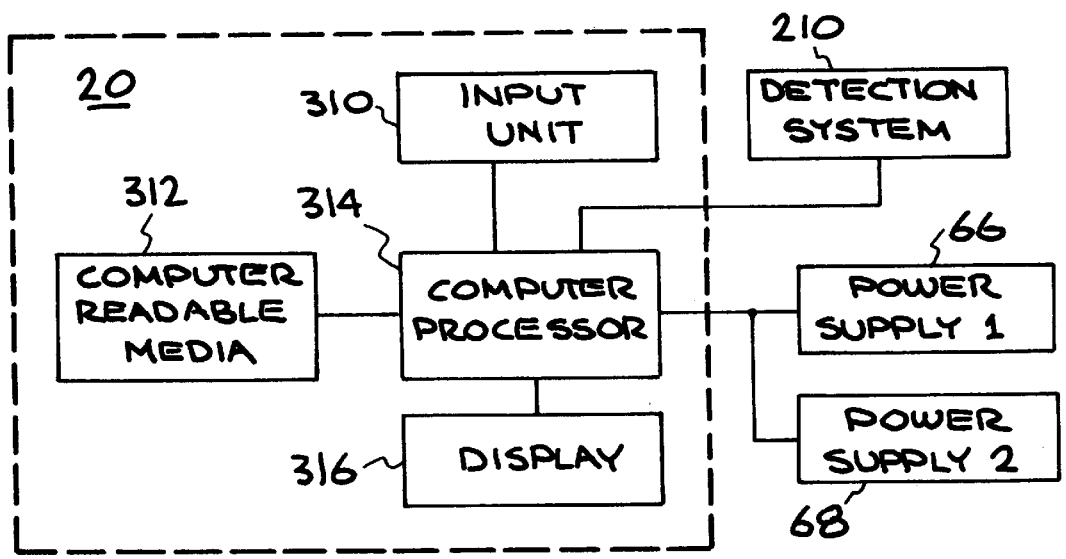
FIG. 2 is a schematic view of the controller hardware and interaction with the solvent gradient delivery system components.

Referring now to FIG. 1, an exemplary embodiment of a liquid delivery system 10 for delivering precisely a liquid having varying composition at low flow rates, employs a controller 20 with software designed for controlling the generation of multiple electro-osmotic flows that are mixed in mixing volume 48 to form a dynamic gradient solution that can be supplied to a receiving means, preferably a column 26.

A. Gradient Flow Delivery System

As shown in FIG. 1, the liquid delivery system 10 comprises a connector 48 that serves as a mixing volume for at least two solutions 36 and 42 in communication with two delivery arms 32 and 34. First delivery arm 32 is placed in communication with first solution 36, which is desirably stored in first solution reservoir 38. Second delivery arm 34 is placed in communication with second solution 42, which is desirably stored in second reservoir 44. To facilitate communication between a receiving means, here column 26, and the two delivery arms 32 and 34, connector 48 is preferably provided comprising a first inlet orifice 50a through which first delivery outlet 52 of first delivery arm 32 extends and attaches. Connector 48 further includes second inlet orifice 50b through which second delivery outlet 53 of second delivery arm 34 extends and attaches. Column inlet end 56 of column 26 connects to connector 48 through outlet orifice 54. In the embodiment shown, connector 48, also referred to as the mixing connector or T-connector, has a T-shape which here conveniently provides three orifices 50a, 50b, 54 for attachment. Column 26 is connected to outlet portion 58 that is desirably in communication with outlet reservoir 60.

As schematically illustrated in FIG. 1, controller 20 is connected via a first control line or wiring 62 to a first means for generating a plurality of voltage programs, such as a variable high voltage power supply 66, or the like, coupled to first solution 36 through first transmission line 72. First diode 73 is desirably provided across first transmission line 72 to restrict the flow of current to one direction. Controller 20 is also connected via a second control line or wiring 64 to a second means for generating a plurality of voltage programs, such as a high voltage power supply 68, or the like, that is coupled to second solution 42 through second transmission line 74. Second diode 75 is desirably provided across second transmission line 74 to restrict the flow of current to one direction. The two voltage sources, here power supplies 66 and 68, desirably have variable output voltages with maximum outputs that are generally about 10–30 kV. In the exemplary embodiment, both power supplies 66 and 68 have a 10–30 kV continuously variable output voltage. Thus, controller 20 and associated variable high voltage power supplies 66 and 68 together comprise means for supplying voltage programs to solutions 36 and 42.

Column 26 is desirably made of fused-silica. Delivery arms 32 and 34 are desirably fused-silica capillary tubes. Connector 48 is desirably made of plastic, such as polytetrafluoroethylene. To assemble delivery arms 32 and 34 and column 26 with connector 48, inlet orifices 50a, 50b and outlet orifice 54 are first prepared, for example, by drilling into plastic connector 48. Outlet 52 of the delivery arm 32 is inserted into inlet orifice 50a, outlet 53 of second delivery arm 34 into inlet orifice 50b, and column inlet end 56 of column 26 into outlet orifice 54. To prevent leakage, the connections formed at orifices 50a, 50b and 54 are preferably sealed, for example, by drops of a UV-cured optical adhesive. The two solutions 36 and 42 combine in connector 48 to form a mixed solution 80 that flows into column 26 and can be used to facilitate separation of samples. Additional solutions through additional delivery arms may be included for mixing in connector 48 to form mixed solution 80, and thus facilitate more complex gradient profiles.

For liquid chromatography application, column 26 is desirably a capillary separation column. Capillary separation column 26 may be open or packed with a stationary phase material for analysis. Various packing methods are available to pack separation column 26. A packed capillary separation column 26 in the exemplary embodiment is advantageously prepared using an electrokinetic packing technique such as that described in U.S. Pat. No. 5,453,163, which is hereby incorporated by reference.

The sizes of delivery arms 32 and 34 and column 26 may vary for the separation of different samples under different conditions. In one example, delivery arms 32 and 34 are capillary arms with an inner diameter of about 50 $\mu$m and column 26 has a 50-$\mu$m or 75-$\mu$m inner diameter. For chromatography applications, separation column 26 can be packed with 3-$\mu$m ODS and 1-$\mu$m silica particles. In some cases, a 5-$\mu$m silica gel is used to make the frit (not shown) for separation column 26.

Solution reservoirs 38 and 44, and outlet reservoir 60 are desirably made of glass or other insulator. A wide variety of miscible solutions 36 and 42 can be delivered using apparatus 10, such as aqueous solutions and pure organic solutions. For liquid chromatography, solutions 36 and 42 are mobile phase solutions. Outlet reservoir 60 is desirably provided to provide an electrical connection and can be used to receive and collect the sample components or eluents that are separated from the sample as it passes through separation column 26.

B. Operation of the Gradient Flow Delivery System

Prior to gradient flow, solution reservoirs 38 and 44 are filled with the desired solutions 36 and 42. A gradient profile is programmed into controller 20 to control gradient flow delivery system 10.

To prepare capillary column 26 for separation in chromatography applications, samples are first introduced electrokinetically into packed capillary separation column 26 by disconnecting it from outlet orifice 54 of mixing connector 48 and placing column inlet end 56 into a sample vial (not shown). An application of about 5 kV for about 5 seconds is generally sufficient to cause the migration of a few nL of the sample into column 26.

Column 26 is then reconnected to mixing connector 48 and the gradient flow delivery process initiated. If capillary separation column 26 is not a packed column a few nL of the sample can be simply siphoned into the column.

To initiate the gradient flow process, controller 20 sends signals to first variable high voltage power supply 66 via control line 62 and second variable high voltage power supply 68 via control line 64, as shown in FIG. 1. First variable high voltage power supply 66 applies a first voltage program governed by controller 20 to first solution 36 while second variable high voltage power supply 68 applies a second voltage program governed by controller 20 to second solution 42. The applied voltages (or voltage programs) generate a first electro-osmotic flow of first solution 36 in first delivery arm 32 and a second electro-osmotic flow of second solution 42 in second delivery arm 34. The first electro-osmotic flow enters mixing connector 48 through inlet orifice 50a while the second electro-osmotic flow enters mixing connector 48 through inlet orifice 50b. The two electro-osmotic flows are mixed as they encounter each other at mixing connector 48 to form mixed solution 80. By controlling the signals from controller 20 to variable high voltage power supplies 6 and 68, the electro-osmotic flows are changed and the composition of mixed solution 80 is varied to form a gradient flow.

Mixed solution 80 exits mixing connector 48 and enters a receiving means, here column 26, via column inlet end 56. For liquid chromatography, the gradient elution generated by the two electro-osmotic flows controlled by controller 20 facilitates the separation of a wide variety of complex samples. The separated components or eluents exit the separation column 26 through the outlet portion 58 to the outlet reservoir 60.

C. Illustrative Experiments

To demonstrate the electro-osmotically driven gradient methodology, the gradient elution technique is adapted to CEC. The mobile phase gradients in CEC can be described as a time function of the concentration, c, of the more efficient eluting component b in the mobile phase at the outlet from the solvent gradient delivery system 10, or more precisely, at column inlet 56 of separation column 26.

This time function may not be identical with the function in the gradient program that is used to control the mixing of two solutions (36 and 42) contained in reservoirs (38 and 44) of gradient elution system 10. This gradient program represents the change in the amount of second mobile phase solution 42 in mixed mobile phase 80 with time. Because mobile phase solutions 36 and 42 are not necessarily the pure components a and b of mixed mobile phase 80, each solution can contain different concentrations of the more efficient eluting agent b in the less efficient component of the mobile phase a. In this instance, the time function of the concentration c of component b can be expressed as $$c=c_1+(c_2-c_1)f(t)$$

where $c_1$ is the concentration of b in solution 36 and $c_2$ is the concentration of b in solution 42 and f(t) ranges from 0 to 1. By choosing various combinations of $c_1$ and $c_2$, different gradient programs can be used to achieve the same solvent gradient.

Simple gradients may differ from one another in three respects: (1) the shape of the gradient (linear, concave, or convex); (2) the slope (steepness) and the curvature of the gradient; and (3) the initial and final concentration of the more efficient component b in the mixed mobile phase 80.

The quality and performance of the solvent gradient delivery system 10 can be evaluated according to the following criteria: (1) accuracy of the gradient formation, i.e., agreement between the actual and the intended gradient profiles; (2) speed of response of the composition of the mixed mobile phase 80 to a change in the applied voltage program; and (3) reproducibility of the gradient profile in repeated runs.

1. Open Column Experiment

For the evaluation of the solvent gradient delivery system 10 in the first experiment, separation column 26 is an open capillary. In this way, the performance of the system itself can be demonstrated by focusing on the composition of the liquid delivered by the system. In this example, open capillary 26 was 26 cm in length and had an inner diameter of 50 μm. First mobile phase reservoir 38 was filled with 55% acetonitrile in 4-mM sodium tetraborate buffer. First variable high voltage power supply 66 was in communication with first mobile phase reservoir 38. Second mobile phase reservoir 44 was filled with 80% acetonitrile in 4-mM sodium tetraborate buffer and was in communication with second variable high voltage power supply 68.

A gradient profile with the following parameters was selected for this demonstration: (1) initial concentration of acetonitrile in the mixed mobile phase 80 was 55% and final concentration was 80% acetonitrile; (2) completion of the gradient in 20 minutes; and (3) one minute hold-up time before gradient elution and 5 minutes hold-up time after the gradient elution. The voltage program used to drive second variable high voltage power supply 68 to achieve this profile is shown in the upper trace of FIG. 3. An inverse program (starting at 20 kV and ramping down to 10.5 kV) of a similar shape was used to drive first variable high voltage power supply 66. The gradient profile (up to 26 minutes) can be described by the following time function of the acetonitrile concentration c:

| | |
|---|---|
| c = 55 | t < 1 |
| c = 55 + 1.25 (t − 1) | 1 < t < 21 |
| c = 80 | 21 < t < 26 | where c is the percentage (v/v) of acetonitrile (b) in the mobile phase, t is the time of gradient, and the slope 1.25 was obtained by dividing the change in concentration by the selected time of the gradient, i.e., (80-55)/20. Although this experiment was performed with a linear voltage ramp, an arbitrary voltage program of any shape can also be used with this system, and the liquid composition will follow very closely.

At the beginning of the gradient run, each delivery arm 32 and 34 was filled with its respective buffer (mobile phase solutions 36 and 42) and separation column 26 was filled with the 55% acetonitrile buffer. Both arms 32 and 34 and separation column 26 were identical in this example (50-μm i.d., 26-cm length) and initial voltage settings of 20 kV in first mobile phase reservoir 38 and 10 kV in second mobile phase reservoir 44 were used. This was expected to result in exclusive feeding to separation column 26 from first reservoir 38, thereby maintaining the composition of separation column 26 at 55% acetonitrile because the voltage at mixing connector 48 should be 10 kV. Holding second mobile phase reservoir 44 at 10 kV should result in no voltage drop and thus no electric field to drive the flow from reservoir 44. In practice, at the beginning of the run, the starting voltage in second reservoir 44 was held at a level slightly higher than 10 kV (e.g., 10.5 kV) to assure that there was no reverse flow during the initial one minute hold-up period.

Figure 3:
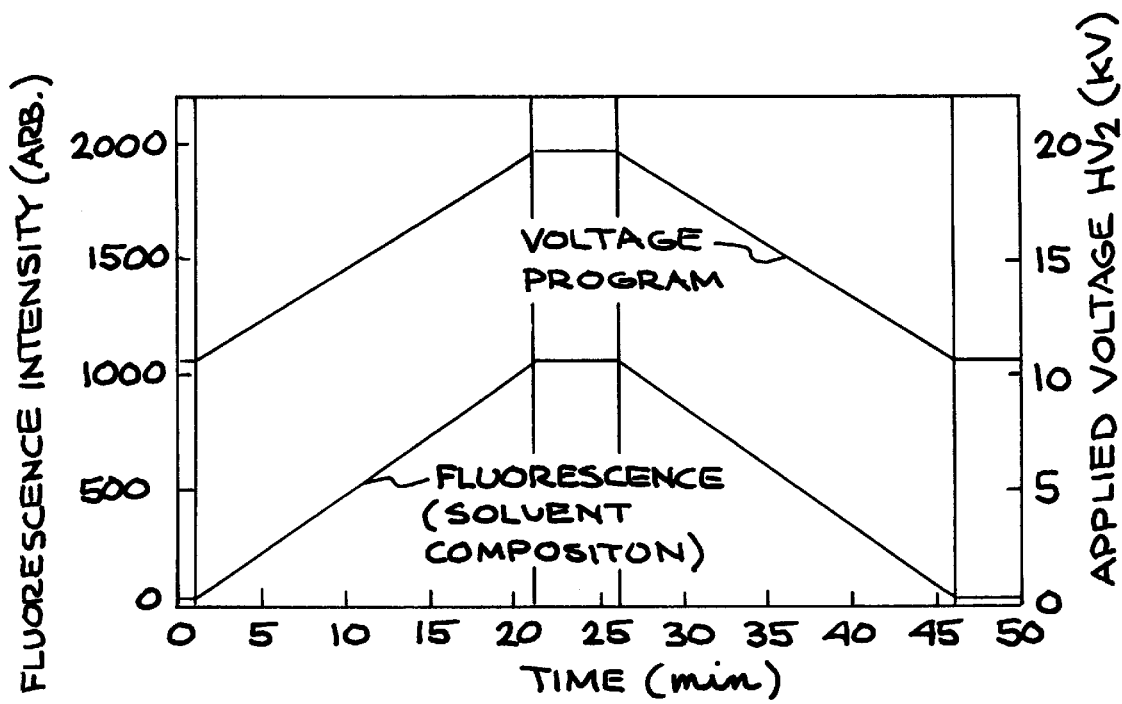
FIG. 3 is a graphic illustration of the response of the solvent gradient delivery system to the input voltage program.

If the conductivity of both buffers of delivery arms 32 and 34 were the same, the voltage at mixing connector 48 would remain constant throughout the gradient run if the sum of the voltages of first variable high voltage power supply 66 and second variable high voltage power supply 68 was maintained at 30.5 kV. Since the conductivity of the two buffers of delivery arms 32 and 34 was not the same, the voltage at mixing connector 48 (and thus the voltage across separation column 26) varies slightly. After the one minute hold-up time, gradient elution was started by applying a voltage program to solutions 36 and 42 comprising simultaneously decreasing the voltage of first variable high voltage power supply 66 and increasing the voltage of second variable high voltage power supply 68 in a linear fashion, as shown in FIG. 3. The gradient elution proceeded with a slope of the voltage program of 0.475 kV/min in each delivery arm 32 and 34 according to the preset program and completed in 20 minutes when the voltage of second variable high voltage power supply 68 reached 20 kV with a positive slope, and the voltage of first variable high voltage power supply 66 reached 10.5 kV with a negative slope. The potential across first delivery arm 32 from the voltage of first variable high voltage power supply 66 was approximately 0.5 kV at this time and, therefore, the mobile phase containing 80% acetonitrile driven by the voltage of second variable high voltage power supply 68 was dominant.

A fluorescent tracer (not shown) was added to second mobile phase reservoir 44 to indicate the amount of second mobile phase solution 42 entering separation column 26. The level of this second mobile phase solution 42 was monitored using laser-induced fluorescence about 2 cm downstream from mixing connector 48, near column inlet 56 of separation column 26. The lower trace of FIG. 3 is the actual experimental profile of the gradient as indicated by the fluorescent tracer. These results show that mixed mobile phase 80 follows closely the voltage program. The electro-osmotic flow rate in liquid delivery system 10, measured using the baseline disturbance caused by an injection of a buffer mixture with a slightly different acetonitrile concentration, was approximately 70 nL/min (linear velocity of 0.6 mm/sec). The gradient delay time originating from the dead volume of mixing connector 48 and capillary tubing 26 between mixing connector 48 and the detection point (not shown) was approximately 30 seconds. The time response is fast, with almost all the delay time resulting from the transit time from mixing connector 48 where the mixing occurs to the detection point about 2 cm downstream from mixing connector 48.

As an indication of the response time of the liquid delivery system 10, the time between the beginning of the linear portion of the voltage program and the onset of the increase in measured fluorescence was measured. From three consecutive runs the relative standard deviation (RDS) of this time interval was found to be less than 1%.

2. Packed Column Experiment

To demonstrate the performance of electro-osmotically driven gradient elution in CEC, a standard mixture of 16 polycyclic aromatic hydrocarbons (PAHs) was separated in less than 90 minutes. This mixture was a standard reference material, SRM 1647c, from the National Institute of Standards and Technology. Delivery arms 32 and 34 in this experiment had an inner diameter of about 50 μm. The length of first delivery arm 32 in liquid delivery system 10 was desirably chosen in such a way that first delivery arm 32 when filled with first mobile phase solution 36 had about the same electrical resistance as that measured in the separation column 26 when filled with the same mobile phase solution 36. The length of second delivery arm 34 was also desirably chosen to have about the same electrical resistance as that in separation column 26 when both were filled with the same second mobile phase solution 42. The voltage program was similar to that described in regard to the open column experiment, except that the initial voltages were changed to 15 kV for first variable high voltage power supply 66 and 30 kV for second variable high voltage power supply 68.

Figure 4:
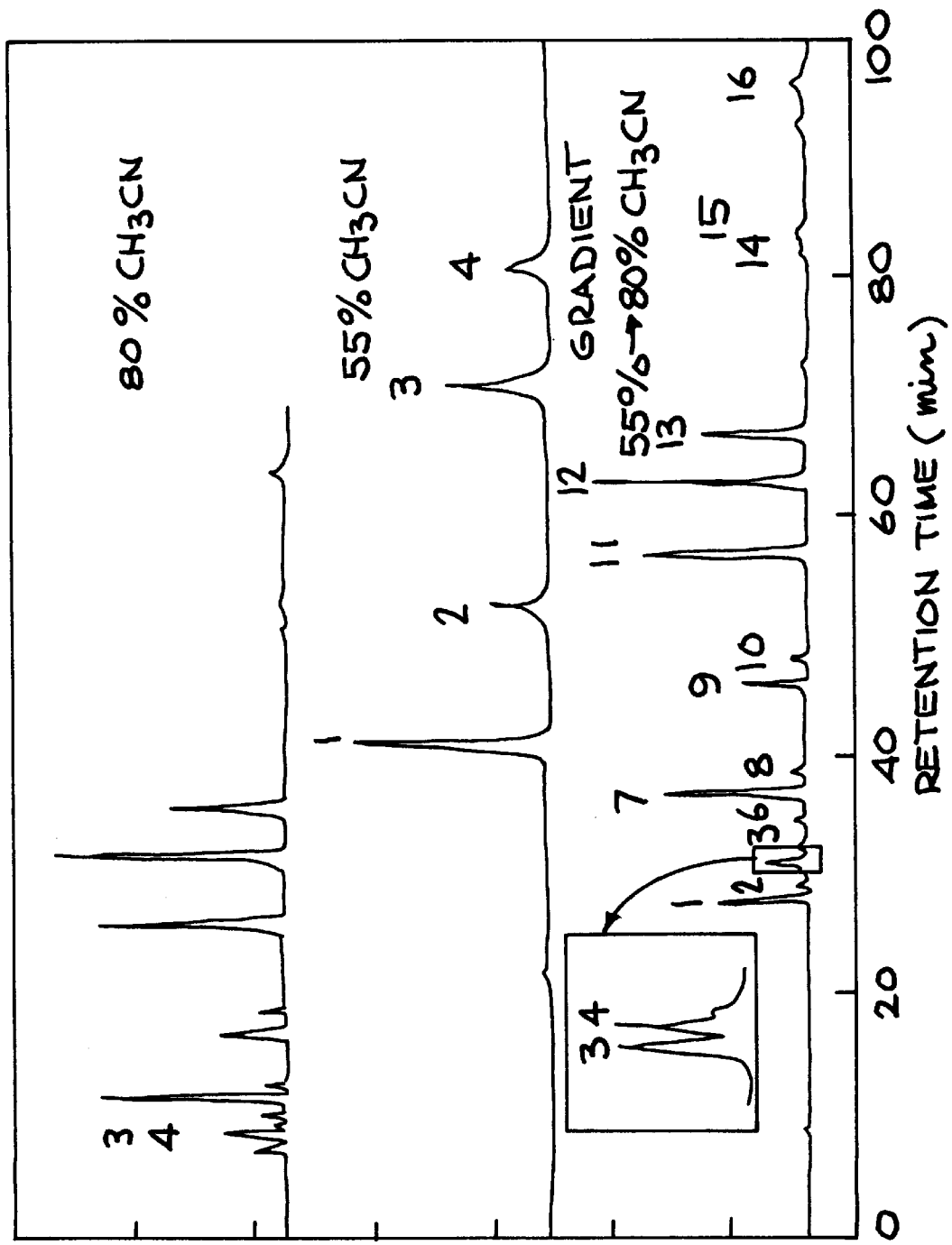
FIG. 4 is a graphic illustration of the result of the separation of sixteen EPA priority pollutants (polycyclic aromatic hydrocarbons) using the solvent gradient delivery system.

FIG. 4 illustrates the performance of the gradient elution in CEC. The top two electrochromatograms are isocratic separations. The top trace shows unresolved separation of peaks 3 and 4 in an isocratic run at 80% acetonitrile mobile phase composition. In the second trace, an isocratic run at 55% acetonitrile resolved the first four peaks very well, but total analysis time is too long to be practical for analyzing all 16 components of the mixture. The bottom trace shows the separation of the sixteen PAHs using the voltage program described above in reference to the open column experiment. All sixteen PAHs were resolved within 90 minutes. The trend of the gradient profile observed in the packed column CEC experiment was similar to that obtained with an open capillary 26.

The experiments show that adapting the gradient elution technique of this invention to a capillary electrochromatography (CEC) system that has a robust gradient elution capability for varying the composition of the mixed mobile phase 80 during separation, permits separation and analysis of a wide variety of complex samples.

In summary, the present novel invention is useful generally in any application where precise delivery of liquids of controlled composition at low flow rates is required. Although the preferred embodiment focuses on CEC, it is understood that the present invention is applicable to other miniature-column-based chemical analysis systems such as pH- and ionic-strength gradients in capillary electrokinetic separations and capillary electrophoresis, micellar electrokinetic capillary chromatography, isotachophoresis, and isoelectric focusing.

It will be understood that the above described arrangements of apparatus and the methods therefrom are merely illustrative of applications of the principles of this invention and many other embodiments and modifications may be made without departing from the spirit and scope of the invention as defined in the claims.

SEQUENCE LISTING

Not Applicable.

We claim:

1. A system for controlling precisely the composition and delivery of a liquid at low flow rate, the system comprising:
   a) at least two miscible solutions, each of said solutions comprising at least one elutriating component;
   b) a mixing connector comprising at least two inlet orifices and at least one outlet orifice, said mixing connector for mixing said miscible solutions;
   c) at least two solution delivery arms, said delivery arms including an inlet and an outlet, each of said inlets in fluid communication with each of said solutions, each of said outlets connected to one of said mixing connector inlet orifices, said delivery arms for delivering said solutions into said mixing connector for mixing, said mixed solution output through said connector output orifice;
   d) at least one receiving means for receiving said mixed solution, said receiving means including an inlet and an outlet, said receiving means inlet connected to said mixing connector outlet orifice, said receiving means outlet in fluid communication with each of said solutions;
   e) means for establishing separate high voltage potentials between each one of said solutions and said receiving means outlet; and
   f) means for independently programming and controlling each of said high voltage potentials, said programming and controlling means for creating and establishing a separate, time-dependent voltage profile between each of said solutions and said receiving means outlet, said time dependent voltage profile causing a corresponding time dependent flow rate profile in each of said solutions entering said mixing connector thereby establishing a controllable solution composition gradient output to said receiving means.

2. The system of claim 1, wherein said solutions include aqueous solutions.

3. The system of claim 1, wherein said means for establishing further comprises a plurality of variable high voltage power supplies capable of providing voltages of about 0–30 kilovolts.

4. The system of claim 3, wherein each variable high voltage power supplies produces a voltage potential sufficient to generate an electroosmotically driven flow through each delivery arm and into said receiving means.

5. The system of claim 4, wherein at least one of the voltage potentials is increasing while at least one other of the voltage potentials is decreasing.

6. The system of claim 1, wherein said delivery arm includes a capillary tube.

7. The system of claim 1, wherein said receiving means includes a column.

8. The system of claim 7, wherein the column is a fused-silica capillary separation column electrokinetically packed with a high-performance liquid-chromatography stationary phase.

9. An electro-osmotically driven gradient system comprising:
   a) at least two solutions;
   b) means, in communication with each solution, for generating a plurality of voltage programs, wherein each of said voltage programs comprise a separate time-variant high voltage potential, and wherein further each of said solutions is associated with one of said voltage programs, each of said associated voltage programs applied to each of said solutions to produce a dynamic electro-osmotic flow in each said solution;
   c) means for mixing the dynamic electro-osmotic flows from each solution to form a dynamic gradient solution; and
   d) means for receiving the dynamic gradient solution.

10. The electro-osmotically driven gradient system of claim 9, wherein said means for generating a plurality of voltage programs comprises a plurality of variable high voltage power supplies in communication with at least one programmable voltage controller.

11. The electro-osmotically driven gradient system of claim 9, wherein said means for generating voltage programs produces a dynamic electroosmotic flow from each solution at sub-$\mu$L/minute dynamic flow rates.

12. A method for delivering a precise quantity of a liquid with variable composition at low flow rates comprising the steps of:
   a) generating a plurality of voltage programs;
   b) applying the plurality of voltage programs to a plurality of solutions to generate a plurality of dynamic gradient profile flows from each of said plurality of solutions; and
   c) merging the plurality of dynamic gradient profile flows to produce a liquid having a variable composition.

13. The method of claim 12, wherein the step of applying said plurality of voltage programs generates a plurality of electro-osmotic flows from each of the plurality of solutions at sub-$\mu$L/minute dynamic flow rates.

* * * * *